United States Patent
Schmitt

(10) Patent No.: US 12,153,060 B2
(45) Date of Patent: Nov. 26, 2024

(54) DEVICE AND METHOD FOR EXTRACTING AND ASPIRATING ACTIVE SUBSTANCES, ESPECIALLY FROM THE CANNABIS PLANT

(71) Applicant: Fritz Schmitt, Luxembourg (LU)

(72) Inventor: Fritz Schmitt, Luxembourg (LU)

(73) Assignee: LUXCAN INNOVATIONS S.A., Luxembourg (LU)

( * ) Notice: Subject to any disclaimer, the term of this patent is extended or adjusted under 35 U.S.C. 154(b) by 674 days.

(21) Appl. No.: 17/421,068

(22) PCT Filed: Dec. 10, 2019

(86) PCT No.: PCT/DE2019/101068
§ 371 (c)(1),
(2) Date: Jul. 7, 2021

(87) PCT Pub. No.: WO2020/143865
PCT Pub. Date: Jul. 16, 2020

(65) Prior Publication Data
US 2022/0095681 A1 Mar. 31, 2022

(30) Foreign Application Priority Data

Jan. 7, 2019 (DE) .................... 10 2019 000 016.1
Jan. 7, 2019 (DE) .................... 10 2019 000 018.8
Jan. 15, 2019 (DE) .................... 10 2019 000 199.0

(51) Int. Cl.
*G01N 33/52* (2006.01)
*A24F 7/04* (2006.01)
(Continued)

(52) U.S. Cl.
CPC ............. *G01N 33/948* (2013.01); *A24F 7/04* (2013.01); *A24F 40/30* (2020.01); *A24F 40/42* (2020.01);
(Continued)

(58) Field of Classification Search
CPC .......... A24F 40/30; A24F 40/42; A24F 40/57; A24F 40/465; A24F 42/10
See application file for complete search history.

(56) References Cited

U.S. PATENT DOCUMENTS 10,512,706 B2 * 12/2019 Avidor .................... A23L 27/00
2014/0366898 A1 * 12/2014 Monsees ................. A24F 40/30
131/329

(Continued)

FOREIGN PATENT DOCUMENTS

CN          205648930 U      10/2016
WO     WO-2014150826 A1      9/2014
(Continued)

OTHER PUBLICATIONS

International Search Report (English and German) and Written Opinion (German) of the International Searching Authority issued in PCT/DE2019/101068, mailed Apr. 21, 2020; ISA/EP.

*Primary Examiner* — Oscar C Jimenez
(74) *Attorney, Agent, or Firm* — Harness, Dickey & Pierce, P.L.C.

(57) ABSTRACT

The invention relates to a capsule for use in a vaporizer, having at least one first cavity formed at least in part by a lid, side walls and bottom of the capsule, and a vaporizable active substance accommodated in the first cavity of the capsule, wherein the side walls and/or the bottom are at least in sections double-walled with an inner wall facing the first cavity of the capsule and an outer wall facing the outside of the capsule, so that at least one second cavity is formed between the inner wall and the outer wall of the capsule, inner wall facing the first cavity of the capsule and an outer wall facing the outside of the capsule, so that at least one second cavity is formed between the inner wall and the outer wall, wherein an auxiliary substance, preferably a further active substance, a chemical reactant and/or a flavoring (Continued)

Figure 1:
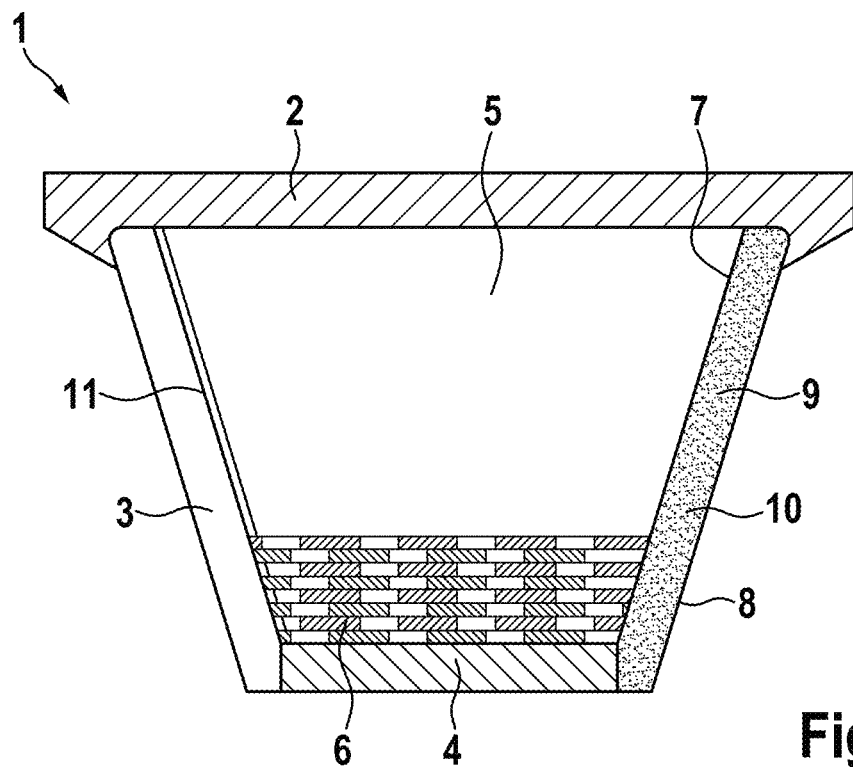

agent is accommodated in the second cavity. A corresponding vaporizer as well as a corresponding vaporizer system are further described.

40 Claims, 10 Drawing Sheets

(51) Int. Cl.
| | |
|---|---|
| A24F 40/30 | (2020.01) |
| A24F 40/42 | (2020.01) |
| A24F 40/465 | (2020.01) |
| A24F 40/51 | (2020.01) |
| A24F 40/57 | (2020.01) |
| A24F 42/10 | (2020.01) |
| A24F 47/00 | (2020.01) |
| A61J 3/10 | (2006.01) |
| A61K 36/185 | (2006.01) |
| A61M 11/02 | (2006.01) |
| A61M 11/04 | (2006.01) |
| A61M 15/00 | (2006.01) |
| B01L 3/00 | (2006.01) |
| B30B 11/04 | (2006.01) |
| B30B 15/30 | (2006.01) |
| G01N 33/94 | (2006.01) |

(52) U.S. Cl.
CPC ........... *A24F 40/465* (2020.01); *A24F 40/51* (2020.01); *A24F 40/57* (2020.01); *A24F 42/10* (2020.01); *A24F 47/00* (2013.01); *A61J 3/10* (2013.01); *A61K 36/185* (2013.01); *A61M 11/02* (2013.01); *A61M 11/047* (2014.02); *A61M 15/0021* (2014.02); *A61M 15/0028* (2013.01); *B01L 3/502* (2013.01); *B01L 3/52* (2013.01); *B01L 3/523* (2013.01); *B30B 11/04* (2013.01); *B30B 15/302* (2013.01); *G01N 33/52* (2013.01); *A61M 11/041* (2013.01); *A61M 2205/3368* (2013.01); *A61M 2205/3686* (2013.01); *A61M 2205/6054* (2013.01); *A61M 2205/6072* (2013.01); *A61M 2205/609* (2013.01); *A61M 2205/75* (2013.01); *A61M 2206/20* (2013.01); *B01L 2300/069* (2013.01); *B01L 2300/0835* (2013.01); *B01L 2300/168* (2013.01); *B01L 2300/1816* (2013.01)

(56) References Cited

U.S. PATENT DOCUMENTS

| | | | |
|---|---|---|---|
| 2017/0055574 A1 | 3/2017 | Kaufman et al. | |
| 2017/0150753 A1 | 6/2017 | Macko | |
| 2018/0027883 A1 | 2/2018 | Zuber et al. | |
| 2018/0029782 A1* | 2/2018 | Zuber | B05B 9/0822 |
| 2018/0132534 A1* | 5/2018 | Reevell | A24F 40/485 |
| 2019/0045833 A1* | 2/2019 | Saygili | A24F 40/30 |
| 2020/0022417 A1* | 1/2020 | Atkins | A61M 15/0063 |
| 2020/0107572 A1* | 4/2020 | Marques Borges | A24F 40/46 |
| 2020/0146360 A1* | 5/2020 | Rosser | A24F 40/42 |
| 2020/0261653 A1 | 8/2020 | Schmitt | |
| 2020/0353171 A1 | 11/2020 | Schmitt | |
| 2020/0360611 A1 | 11/2020 | Schmitt | |
| 2022/0183364 A1* | 6/2022 | Trawi | A24F 40/90 |
| 2023/0232899 A1* | 7/2023 | Zominy | A24F 40/42 |
| | | | 131/329 |

FOREIGN PATENT DOCUMENTS

| | | |
|---|---|---|
| WO | WO-2017108987 A1 | 6/2017 |
| WO | WO-2017207674 A1 | 12/2017 |
| WO | WO-2019105811 A1 | 6/2019 |

* cited by examiner

DEVICE AND METHOD FOR EXTRACTING AND ASPIRATING ACTIVE SUBSTANCES, ESPECIALLY FROM THE CANNABIS PLANT

CROSS-REFERENCE TO RELATED APPLICATIONS

This application is a U.S. National Phase Application under 35 U.S.C. 371 of International Application No. PCT/DE2019/101068, filed on Dec. 10, 2019, which claims the benefit of German Application No. 10 2019 000 0199.0, filed on Jan. 15, 2019, and German Application No. 10 2019 000 016.1, filed on Jan. 7, 2019, and German Application No. 10 2019 000 018.8, filed on Jan. 7, 2019. The entire disclosures of the above applications are incorporated herein by reference.

BACKGROUND

This section provides background information related to the present disclosure which is not necessarily prior art.

Technical Field

The invention relates to a capsule for use in a vaporizer, having at least a first cavity formed at least in part by a lid, side walls and bottom of the capsule, and a vaporizable active ingredient received in the first cavity of the capsule. The invention further relates to a vaporizer, preferably a hand-held vaporizer, and to a system comprising a vaporizer and a capsule received in the vaporizer. In particular, devices and methods for extracting and aspirating active ingredients from the cannabis plant are also described.

Discussion

Vaporizers have been used for many decades in medicine and naturopathy, especially for diseases of the lungs and respiratory tract as well as in pain therapy. Since the active ingredients are absorbed through the lungs, an effect is felt relatively quickly.

In classic aromatherapy, essential oils from plant extracts or medicinal herbs such as chamomile, sandalwood or rosemary are vaporized. In contrast, in phytotherapy, for example, plant extracts are vaporized, whereby each active ingredient has a different boiling point and accordingly requires a certain temperature in order to develop its optimal effect. Compared to vaporizing essential oils, direct vaporization of herbs is more economical and efficient.

When cannabis is used for medicinal purposes, as many cannabinoids as possible, such as THC and CBD, should be released from the cannabis plant. However, the cannabinoids in the cannabis plant are not present in their pure form, but as carboxylic acids such as THCA and CBDA, which must be converted to THC and CBD. This is achieved by the decarboxylation process, in which heat is used to split off one molecule of carbon dioxide from each of the carboxylic acids, leaving the compounds THC and CBD. The heat required for this can be provided by vaporization or combustion of the active ingredient or the cannabis plant or herb.

Combustion is usually understood to be a release of chemically bound energy into heat through material conversion. In this process, fuel and oxygen as starting materials of the reaction, so-called reactants, are converted into end products such as carbon dioxide and water in a sequence of chemical reactions. During the course of these reactions, which are also referred to as chain reactions, intermediate products such as carbon monoxide are formed; in addition, pollutants such as nitrogen monoxide and soot can also occur. The reaction rates of the elementary reactions, in particular the chain branching reactions that maintain combustion, are temperature-dependent, among other things, i.e. stable combustion can only occur when a temperature dependent on the fuel, among other things, is exceeded.

When cannabis is burned or smoked, the embers generate heat between 800 and 900° C., which is sufficient to convert the carboxylic acid THCA into THC. However, approximately 88% of the substances produced during combustion do not contain cannabinoids; a majority of cannabinoids are destroyed by combustion or the high temperature. In addition, burning cannabis with an open flame and high temperatures releases harmful chemicals, such as tar, benzene, or carbon monoxide.

When vaporizing cannabis, on the other hand, a temperature of over 185 degrees Celsius should be aimed for. The carboxylic acids and terpenes are almost completely dissolved out at a temperature of 210 degrees Celsius without the plant material burning. Vaporizing cannabis also does not produce the toxic substances released during combustion, as the cannabis is heated only to the point at which the cannabinoids convert to gas. This point is usually around 200° C.

Vaporizing the active ingredient, e.g. a cannabis flower, offers further decisive advantages. Thus, a large amount of the ingredients can be absorbed during inhalation; the onset of action takes place after only one to two minutes and can last for two to four hours. Studies show that up to one-third of the cannabinoids from cannabis are absorbed into the blood when inhaled, whereas only one-ninth is absorbed when cannabis medications or cannabis extracts are taken orally, for example. In addition, there is a rapid onset of action within a few minutes, while oral ingestion of cannabis medications or cannabis extracts can take up to 90 minutes for the onset of action. Because absorption of the active ingredients into the bloodstream is rapid, it is easy to find the right dosage. This is especially helpful during initial applications. For example, a patient can slowly approach the dosage recommended by the doctor. Furthermore, the vapor odor produced by the vaporizer is very mild and short-lived.

A well-known handheld vaporizer is marketed by the company Storz & Bickel under the name "Mighty Medic". The user can fill herbs, especially ground cannabis leaves or hemp flowers, into reusable capsules and thereby dose the filling level himself. The capsule has a simple wall; the lid is designed as a sieve. Before use in the vaporizer, the manually filled capsules must be stored in a separate capsule magazine to protect the capsules or the ground cannabis leaves or hemp flowers contained in the capsules from environmental influences and contamination.

On the one hand, this results in awkward storage of the filled capsules; the active ingredients inside the capsule can diffuse into the environment or volatilize, so that the shelf life of the active ingredients is limited. On the other hand, when the capsules are stored or removed from the capsule magazine, germs, impurities, dust, or the like can enter the capsules, even if the capsule magazine itself should be free of germs, impurities, or the like. Germs or the like can also enter the capsule interior due to the multiple use of the capsule. In addition, the manual filling of the capsule can result in incorrect dosages or the fill level can vary. In particular, if different active ingredients are to be vaporized in the capsule, or if several substances are to interact in a certain way, manual filling is disadvantageous, since not only the respective quantity but also the mixing can be relevant.

SUMMARY

This section provides a general summary of the disclosure, and is not a comprehensive disclosure of its full scope or all of its features.

It is therefore one aspect of the present invention to provide a capsule that provides increased hygiene and improved capsule functionality.

Accordingly, the side walls and/or the bottom are formed double-walled at least in sections with an inner wall facing the first cavity of the capsule and an outer wall facing the outside of the capsule, so that at least one second cavity is formed between the inner wall and the outer wall, wherein an excipient, preferably a further active ingredient, a chemical reactant, and/or a flavoring agent is accommodated in the second cavity. The further active ingredient may be different from or similar to the active ingredient accommodated in the first cavity of the capsule. It may be provided that the further active ingredient may enhance the effect of, or interact with, the active ingredient received in the first cavity. The chemical reactant may be provided to release heat by chemical reaction. The adjuvant may be vaporizable.

The active ingredient may be or comprise a plant-based active ingredient. The chemical reactant may be or comprise, for example, an acid anhydride or an acid salt and a basic anhydride or a basic salt, or a mixture thereof. The basic salt may be selected from the group consisting of or comprising sodium acetate, sodium benzoate, and potassium ascorbate. The flavoring agent may be or comprise, for example, a flavoring agent, a flavor enhancer, a fragrance, or the like.

If reference is made in the following to the active ingredient, the active ingredient and/or the excipient may also be meant.

In particular, provision can be made for the capsule to be designed as a one-way capsule. This means that the composition of the active ingredient in the first hollow chamber and of the excipient accommodated in the second hollow chamber can be predetermined during capsule production. This may facilitate the manageability of the capsule by the user. It may be envisaged to provide different concentrations and/or combinations of the respective active ingredients for certain areas of application of the capsule.

Several separate cavities may also be formed between the inner wall and the outer wall. Provision may also be made to divide or partition the first cavity into a plurality of sub-cavities, which may be separate and/or self-contained. The term "double-walled" may also include, at least in sections, multi-walled side walls and/or bottom. For example, a double-walled sidewall may include an inner wall facing the first cavity, an outer wall facing the exterior of the capsule, and at least in sections, one or more intermediate walls disposed between the inner wall and the outer wall. A plurality of intermediate cavities may be formed.

The side walls, the inner wall, the outer wall, the lid and/or the bottom of the capsule may be or comprise a plastic, a ceramic, a glass or a metal. The lid of the capsule may be or comprise a film. This can ensure a hygienic active ingredient inside the capsule and an accurate dosage from the production of the capsules to their use in the vaporizer.

The outer wall, lid and bottom may be air impermeable so that the first and/or second cavity may be hermetically sealed from an environment of the capsule. It may be provided that the lid is sealed to the side walls. Since the cavities are hermetically sealed from the environment, the active ingredient and/or the excipient may be present in solid, liquid and/or gaseous form in the capsule. In addition, impurities of the active ingredient received in the capsule are prevented or at least significantly reduced, handling and storage are facilitated, and a longer shelf life of the active ingredient is achieved. In particular, the capsule can advantageously be designed as a one-way capsule.

The first and/or the second cavity can either be evacuated or at least partially filled with an inert gas. The evacuation or the vacuum or the inert gas atmosphere in the cavity can increase the shelf life of the active ingredient. In particular, the capsule can be stored for a long period of time without affecting the efficacy of the active ingredient contained in the capsule. In addition, this may facilitate evaporation and/or prevent combustion in the absence of oxygen. Alternatively or additionally, it may also be provided that the first and/or the second cavity is filled with compressed air or a propellant gas.

The inner wall of the side wall arranged between the first and second cavity can be perforable, porous and/or semi-permeable and/or have predetermined breaking points. This may provide for a connection or opening to be made between the first and second cavities in a targeted or controlled manner and/or at a specific time and/or under specific conditions. In some embodiments, however, it may also be provided that the first and second cavities remain fluidically separated from each other during vaporization of the active agent and the excipient, i.e., the active agent and the excipient are vaporized separately. Provision may be made to mix the vaporized substances only after the respective vaporization. In some embodiments, the vaporization of the active ingredient and the excipient may also take place separately in time, one after the other, or at least overlapping in time.

The lid may be perforable and/or have predetermined breaking points and/or valves. This can create an opening in the lid so that the active ingredient accommodated in the first cavity and/or the excipient accommodated in the second cavity can interact with the environment of the capsule or can escape from the capsule.

For example, if the excipient received in the first cavity is vaporized, the vaporized excipient can exit the capsule through the opening in the lid. If the second cavity is open to the first cavity through the inner wall, the vaporized excipient can enter the first cavity and exit the first cavity through the lid. Alternatively or additionally, however, the lid can also be opened in the area of the second cavity so that the auxiliary can exit from the second cavity through the lid.

The active ingredient may be or comprise a cannabis flower, a cannabis oil, a cannabinoid, a cannabis extract, or the like. The active ingredient may be a liquid, a solid, or a gas. Preferably, the active ingredient is a cannabis plant or one or more cannabis leaves or the like. The cannabis plant or cannabis leaves received in the capsule may be humidified. A vaporizer into which the capsule is insertable may include, for example, a microwave generator so that the humidified cannabis plant or cannabis leaves may be heated, for example, to temperatures between 180-220° C. and the active ingredient vaporized.

The bottom of the capsule may comprise, at least on its outer side, at least partially a material, preferably a metal, with a higher thermal conductivity compared to the material of the side wall. If the bottom is double-walled, it may be provided that a thermally conductive material is included between the outer side and the inner side of the bottom facing the first cavity of the capsule. This may provide good heat transfer between the outside of the bottom and the inside.

The lid and/or the bottom may have a coating at least partially on an inner side facing the cavity. Alternatively or additionally, the inner wall may have at least partially a coating. The coating may preferably comprise a chemical reactant, a UV filter and/or a thermochromic material. The chemical reactant may be adapted to release heat during a chemical reaction. The coating may also comprise a complementary chemical agent that reacts with a chemical reactant held in, for example, a reservoir or the second hollow chamber to release heat. The complementary chemical agent may be or comprise, for example, a calcium oxide.

Alternatively or additionally, the outside of the capsule may also be at least partially coated with a UV filter and/or a thermochromic material. The UV filter can, for example, increase the shelf life of the active ingredient or, if applicable, the excipient contained in the capsule. Due to the temperature-dependent color changes of the thermochromic material, this can serve as an indicator of the temperature in the cavity of the capsule or of the active ingredient.

The first cavity may receive one or more grinding balls for grinding the active ingredient. The grinding ball may comprise a ferromagnetic material. A vaporizer into which the capsule can be inserted can have suitable magnets, for example electromagnets, by means of which the grinding balls in the capsule can be moved in a targeted or controlled manner. This allows the active ingredient contained in the capsule to be comminuted. The comminution can increase the surface area of the active ingredient, so that, for example, a better heat transfer can result and/or the evaporation of the active ingredient is facilitated. It may be provided to heat or warm the grinding balls, e.g. by induction heating. The grinding ball may have cut edges or be suitably shaped for improved comminution.

The inner wall and/or the outer wall can consist at least in sections of a glass and/or a transparent plastic. This makes it possible, for example, to easily check the state of the active ingredient from the outside, i.e. from outside the capsule. It may also be provided that the inner wall and/or the outer wall comprise viewing windows or the like. If the outer wall is only transparent in sections, it may be provided that only the transparent sections are coated with a UV filter. If the inner wall and the outer wall have viewing windows or are transparent in sections, provision can be made for the respective viewing windows to be arranged overlapping in such a way that the first cavity is visible from outside the capsule.

A heating coil may be disposed in the first and/or second cavity. The heating coil may comprise one or more coils. The heating coil may alternatively or additionally comprise a heatable metal foil. It may be provided that the heating coil is heated by an electric current. For this purpose, an outer side of the capsule may comprise an electrical contact so that an electrical current can flow through the heating coil. It may also be provided that the heating coil is passed through the capsule wall. The active agent received in the first cavity and/or the excipient received in the second cavity may be in contact with the heating coil, such that the active agent may be heated or heated by the heating coil.

The invention further relates to a vaporizer for vaporizing active ingredients. The vaporizer may comprise a mouthpiece and a vaporizer unit. The vaporizer may comprise a capsule receptacle for receiving a capsule according to the invention, wherein the capsule receptacle may comprise a first capsule opening device and may be fluidically connected to the mouthpiece via the first capsule opening device so that, when the capsule is received, a fluidic connection between a cavity of the capsule and the mouthpiece may be provided by the first capsule opening device, wherein the vaporizer unit may be arranged for vaporizing an active substance located in the cavity of the capsule when the capsule is received. The vaporizer unit may heat or heat the active ingredient to a temperature of 180-220° C., for example.

The vaporizer is preferably a hand-carryable vaporizer, i.e. preferably dimensioned such that it can be comfortably held in a human hand and/or operated with a single hand. By the wording "hand-portable vaporizer" it may be meant that the vaporizer is not fixedly connected but is mobile and/or has dimensions and/or a weight such that it can be held or carried by a human hand.

The first capsule opening device may be adapted to the lid of a capsule to be inserted into the vaporizer to establish a fluidically tight connection between the first and/or second cavity of the capsule and the mouthpiece when the capsule is inserted. For example, the first capsule device may include means for perforating the lid. The first capsule opening device may be tubular and/or have fluid flow therethrough. The first capsule opening device may correspond to one of the end portions of a connecting conduit for fluidly connecting a capsule inserted into the capsule receptacle to, for example, the mouthpiece. The end portion may face the capsule receptacle. It may also be provided that the capsule opening device corresponds to or is identical to the connecting line, at least in sections.

The vaporizer unit may be or include a heating plate in the capsule receptacle so that when the capsule is received, the heating plate may contact an exterior, preferably a bottom, of the capsule.

The vaporizer unit may be or comprise a reservoir for receiving a fluid, wherein the reservoir may be fluidly connected to the capsule receptacle via a second capsule opening device such that, when the capsule is received, fluid communication may be provided between a cavity of the capsule and the reservoir by the second capsule opening device. The reservoir may be or comprise a replaceable container. However, it may also be provided that the reservoir is a tank housed and/or fixedly mounted in the vaporizer.

The second capsule opening device may be adapted to the lid of a capsule to be inserted into the vaporizer to establish a fluidically tight connection between the reservoir and the first and/or second cavity of the capsule when the capsule is inserted. The second capsule opening device may be tubular and/or flow-through. The second capsule opening device may correspond to an end portion of a connecting conduit for fluidically connecting, for example, the reservoir to a capsule inserted into the capsule receptacle. The end portion may face the capsule receptacle. It may also be provided that the capsule opening device corresponds to or is identical to the connection line, at least in sections.

The vaporizer unit may have one or more heating wires in the reservoir and/or fluidically between the reservoir and the capsule receptacle to heat the fluid. The fluid may be or comprise compressed air or a propellant gas. The fluid may flow over the heating wire and be heated in the process. The fluid thus heated may subsequently enter the first and/or second cavity of the capsule, flow over and/or through the active agent, and transfer heat, for example by convection, to the active agent. It may be envisaged that the fluid is or comprises ambient air. In this case, the reservoir may be open to the environment of the capsule so that ambient air can enter the reservoir or vaporizer, be heated by the heating wire, and subsequently be introduced into the capsule.

Alternatively or additionally, the fluid may be received in the reservoir, wherein the fluid may be or comprise a chemical reactant such that heat may be released by a chemical reaction of the chemical reactant with a complementary chemical agent.

The capsule receptacle, the reservoir and/or the second capsule opening device may comprise, preferably be coated with, the complementary chemical agent such that heat may be released by a chemical reaction of the chemical reaction agent with the fluid. It may also be provided that, alternatively or additionally, when the capsule is received in the capsule receptacle, the capsule comprises the complementary chemical agent. For example, an inner surface of the capsule and/or the first cavity and/or the second cavity may be coated with the complementary chemical agent such that the fluid or chemical reactant introduced into the capsule chemically reacts within the capsule.

The vaporizer unit may be or have a microwave generator. If the active ingredient has, for example, a moistened cannabis leaf, water molecules can be excited by the microwaves and the active ingredient can be heated.

The vaporizer unit can be or have a heating coil in the capsule receptacle. The heating coil may be arranged to contact the outside and/or the bottom of the capsule when the capsule is received in the capsule receptacle. When an electric current is applied to or flows through the heating coil, the heating coil may heat or be heated.

If a heating coil is arranged in the first and/or second cavity of the capsule to be inserted into the vaporizer, or if the capsule has a heating coil, the capsule receptacle of the vaporizer can have suitable electrical contacts so that the heating coil can have electrical flow through it. Preferably, the respective contacts are arranged on the outside of the capsule and the capsule receptacle such that a contact is present when the capsule is inserted in the capsule receptacle.

The vaporizer unit can have any combination of the described vaporizer concepts. For example, the vaporizer unit can have both a heating plate and a heating coil.

The vaporizer may have an actuator, wherein the first and/or optionally the second capsule opening device may have flaps that can be opened when the actuator is actuated. The term "flaps" may also refer to valves or other devices for adjusting a volume flow. Alternatively or additionally, the first and/or optionally the second capsule opening device can be moved in the direction of the capsule receptacle when the actuating element is actuated. It may also be provided that in the case of non-Alternatively or additionally, the vaporizer may comprise pressure sensors by means of which, for example, a pulling or sucking at the mouthpiece can be detected, wherein the flaps can be opened and/or the capsule opening devices can be moved in the case of detected negative pressure and/or pulling at the mouthpiece. It may be provided that when the actuating element is not actuated and/or actuation stops and/or negative pressure is no longer applied by pulling on the mouthpiece, the first and/or second capsule opening devices are moved away from or back into the capsule, so that the capsule opening device no longer protrudes into the interior of the capsule. It can be provided that the lid is closed when the capsule opening device is moved away or back, in particular that it becomes fluid-tight.

Alternatively or additionally, it can be provided that the vaporizer unit is activated when the actuating element is actuated and/or when negative pressure is detected, so that the active substance and/or the excipient is vaporized. The actuating element may be arranged on an outer side of the vaporizer, e.g. on a handle. The actuating element may be or comprise a button, a slider, a push button, a rotary knob, a haptic element or the like.

It may be provided that already during or after insertion of the capsule into the capsule receptacle, a fluidic connection is established between the cavity of the capsule and the mouthpiece by the first capsule opening device and/or, if applicable, between the reservoir and the cavity. For example, the cap of the capsule may be perforated upon movement of the capsule during insertion of the capsule. For example, if the capsule is held in its inserted state by a pivotable capsule holder, e.g., a pivotable plate, in the vaporizer or capsule receptacle, then when the capsule holder is closed, the capsule can be moved in a guided manner such that the lid is perforated, for example, or valves provided on the lid suitably seal with or are connected to tubular connecting lines or the like.

The vaporizer can have a cooling unit fluidically arranged between the capsule receptacle and the mouthpiece, so that active ingredient vaporized by the vaporizer can be cooled, preferably to a temperature of 10-30° C., particularly preferably to a temperature of 15-25° C. For example, the cooling unit may have a cooling coil and/or cooling fins. Convection cooling, for example by air streams or the like, may also be provided. The cooling unit may comprise a fan, ventilator or the like.

The vaporizer can have a reservoir fluidically upstream of the mouthpiece, in which active substance vaporized by the vaporizer can be collected. It can be provided that the reservoir can be heated and/or cooled and/or thermally insulated. This allows a certain amount of already vaporized active ingredient to be kept in reserve so that, for example, interruptions in the vaporization of the active ingredient can be bridged. Depending on the type of vaporizer unit used, there may be a time difference between the start of heating of the active ingredient and the provision of the vaporized active ingredient, which can also be bridged by already vaporized active ingredient stored in the reservoir.

The mouthpiece can have an atomizer for atomizing vaporized active substance and/or excipient into droplets. The diameter of the respective droplets and/or the average diameter of the droplet distribution can be between 0.5 to 500 μm, preferably between 0.5 to 50 μm and particularly preferably between 0.5 to 5 μm. This allows the vaporized and atomized active ingredient and/or excipient or the corresponding aerosol to reach the finest ramifications of the lungs or respiratory tract when inhaled. The nebulizer can be or comprise a nozzle nebulizer, an ultrasonic nebulizer and/or a membrane nebulizer.

The mouthpiece, atomizer, and/or first and/or second capsule orifice device, as applicable, may be or include a venturi nozzle.

The vaporizer may have at least one filter fluidically upstream of the mouthpiece, and the filter may preferably be disposed on the mouthpiece.

The vaporizer may have a control and/or regulation unit and sensors for controlling and regulating the temperature of the vaporizer unit. The control and/or regulating unit may also be provided to control and/or regulate the temperature of the cooling unit. The sensors may be located in the capsule receptacle, the cavities of the capsule, the reservoir, the cooling unit, the vaporizer unit, the reservoir, the mouthpiece, and/or in the respective connecting lines. The sensors can be set up to detect the temperature, the flow rate and/or the volumetric flow, the pressure, the gas composition or the composition of the vaporized active ingredient and to forward these to the control and/or regulation unit. The control and/or regulating unit may comprise a processor, a microcontroller, an integrated circuit, an FPGA, or the like. The vaporizer may have an actuator or controller for adjusting the volumetric flow rate of the vaporized agent. The actuating element or controller may be, for example, a knob, a button, a slider, or the like. The actuating element or the regulator may be arranged on an outside of the vaporizer.

The atomizer may include a labyrinthine channel with at least one breakaway edge so that droplets flowing through the channel can be separated larger than a maximum droplet size.

The vaporizer may include an accumulator, battery, or the like to provide power or energy to the vaporizer unit, sensors, and/or the control and/or regulating unit, or other components housed in the vaporizer that require power.

The vaporizer may include a fingerprint sensor and/or a user identification device. The fingerprint sensor may be arranged on the housing in such a way that, during normal handling in use, or preferably one-handed use, the fingerprint sensor detects and/or is able to detect a fingerprint. For example, the fingerprint sensor may be arranged such that a finger of the same hand rests on the fingerprint sensor during one-handed use of the vaporizer and actuation of the actuation element. This can ensure that only authorized users can use the vaporizer. The information regarding user identification can, for example, be stored in the control and/or regulation unit.

It may be provided that the outside of the lid and or the bottom of the capsule has a code, for example a QR code, an alphanumeric code, a barcode and/or a pictogram, and/or an RFID chip. The pictogram may also be an arrangement, e.g., stringing together, of individual pictograms. However, the code may alternatively or additionally be arranged on a side wall of the capsule. The vaporizer may have a reading unit, wherein the reading unit may be set up to detect and/or read a code, preferably a QR code, an alphanumeric code, and/or a pictogram, and/or an RFID chip, applied to an outer side of the capsule when the capsule is inserted. The reading unit may preferably be arranged in the capsule receptacle. The reading unit may The reading unit may be in data exchange with the control and/or regulation unit. The code may contain, for example, information relating to the active ingredient(s) and/or vaporization temperature accommodated in the capsule. It may be intended to use the information regarding vaporization temperature to control the heating element. If the vaporizer has a fingerprint sensor or other device for user identification, provision may be made to vaporize the active ingredient(s) in the capsule only if the user identified by the fingerprint sensor or otherwise is authorized to do so. The verification of the authorization can be performed, for example, by the control and/or regulation unit by comparison with the user information. The reader unit may be arranged to detect the code optically, e.g. with a camera. The reader unit may be arranged to detect the code optically, e.g. with a camera and optionally an illumination. The reader unit may be set up to read the RFID chip electromagnetically. The term "RFID chip" can also mean an RFID transponder.

The invention further relates to a vaporizer system for vaporizing an active ingredient, comprising a vaporizer according to the invention and a capsule according to the invention received in the capsule receptacle of the vaporizer. The vaporizer system may additionally comprise a charging or docking station for receiving the vaporizer.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 2:
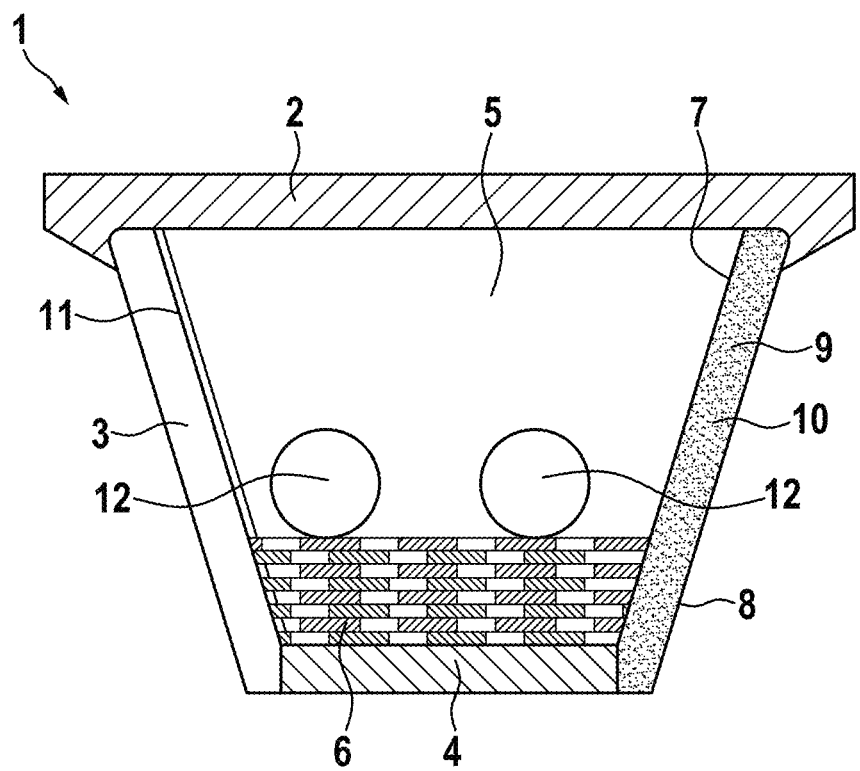
Figure 3:
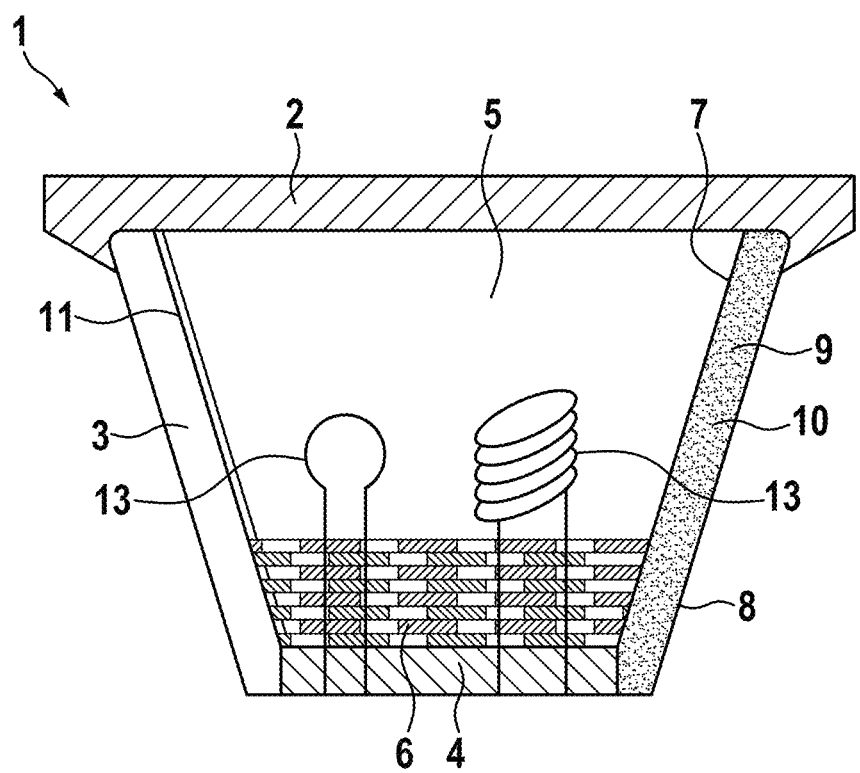
Figure 4:
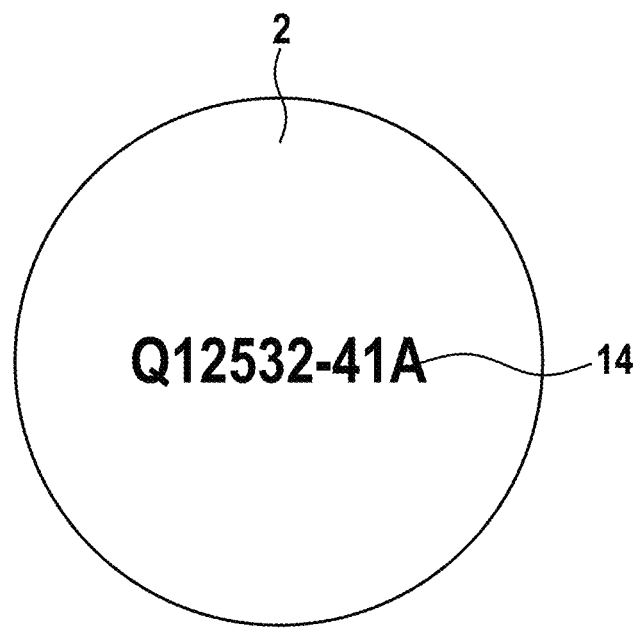
Figure 4:
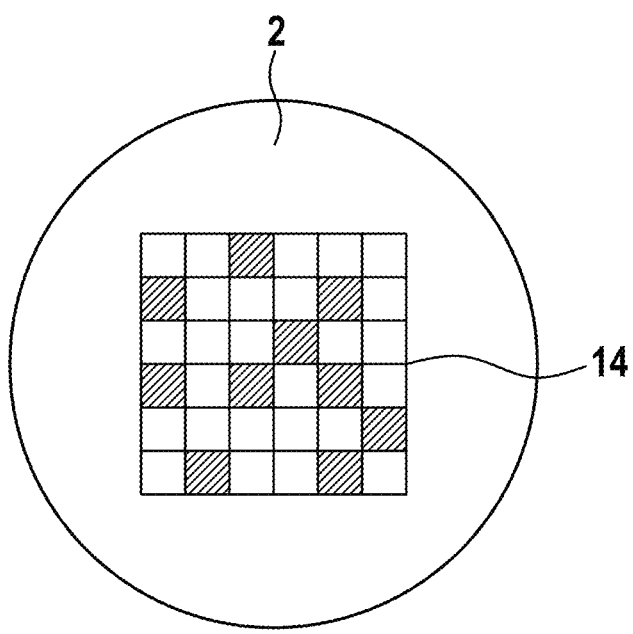
Figure 5:
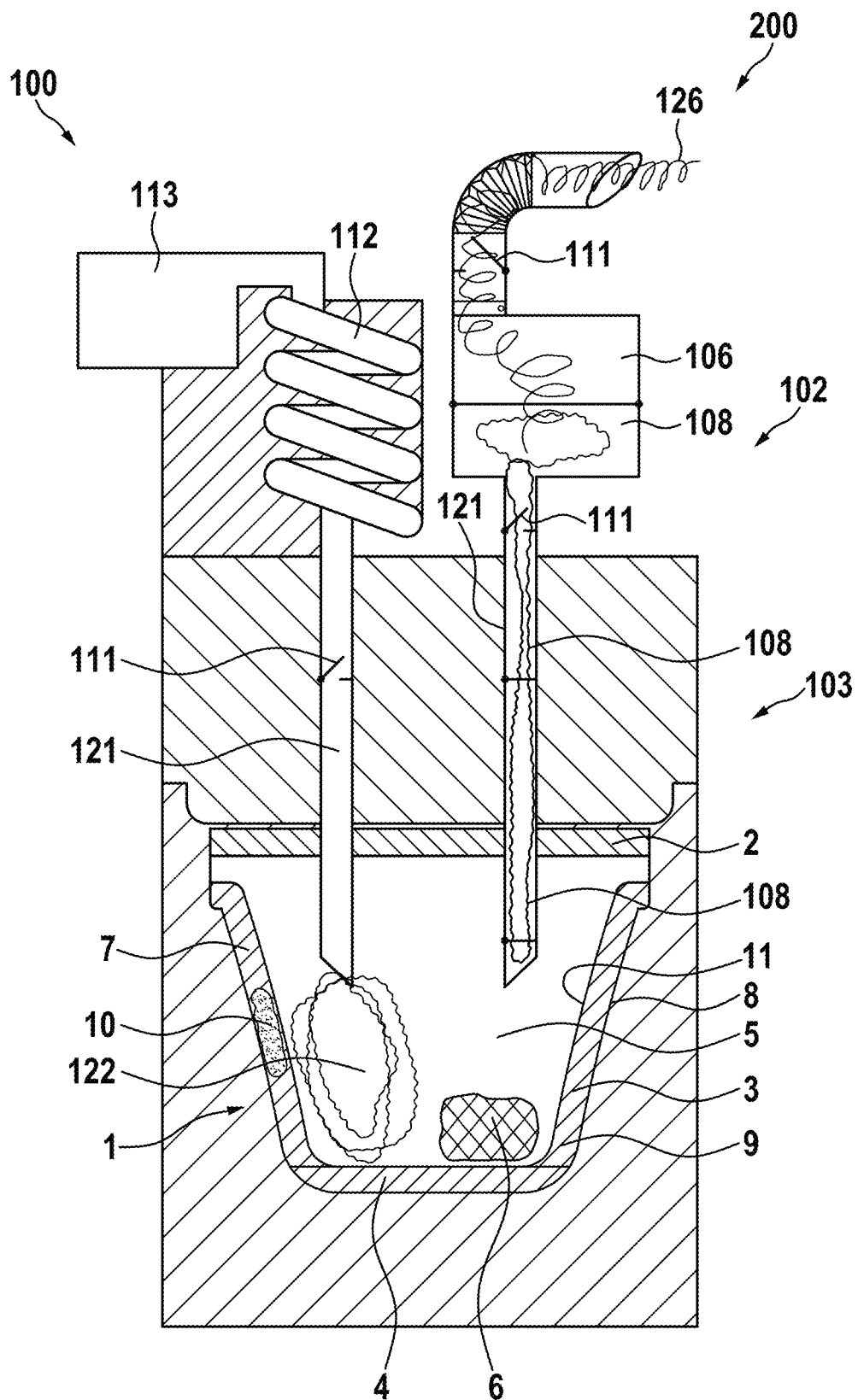
Figure 6:
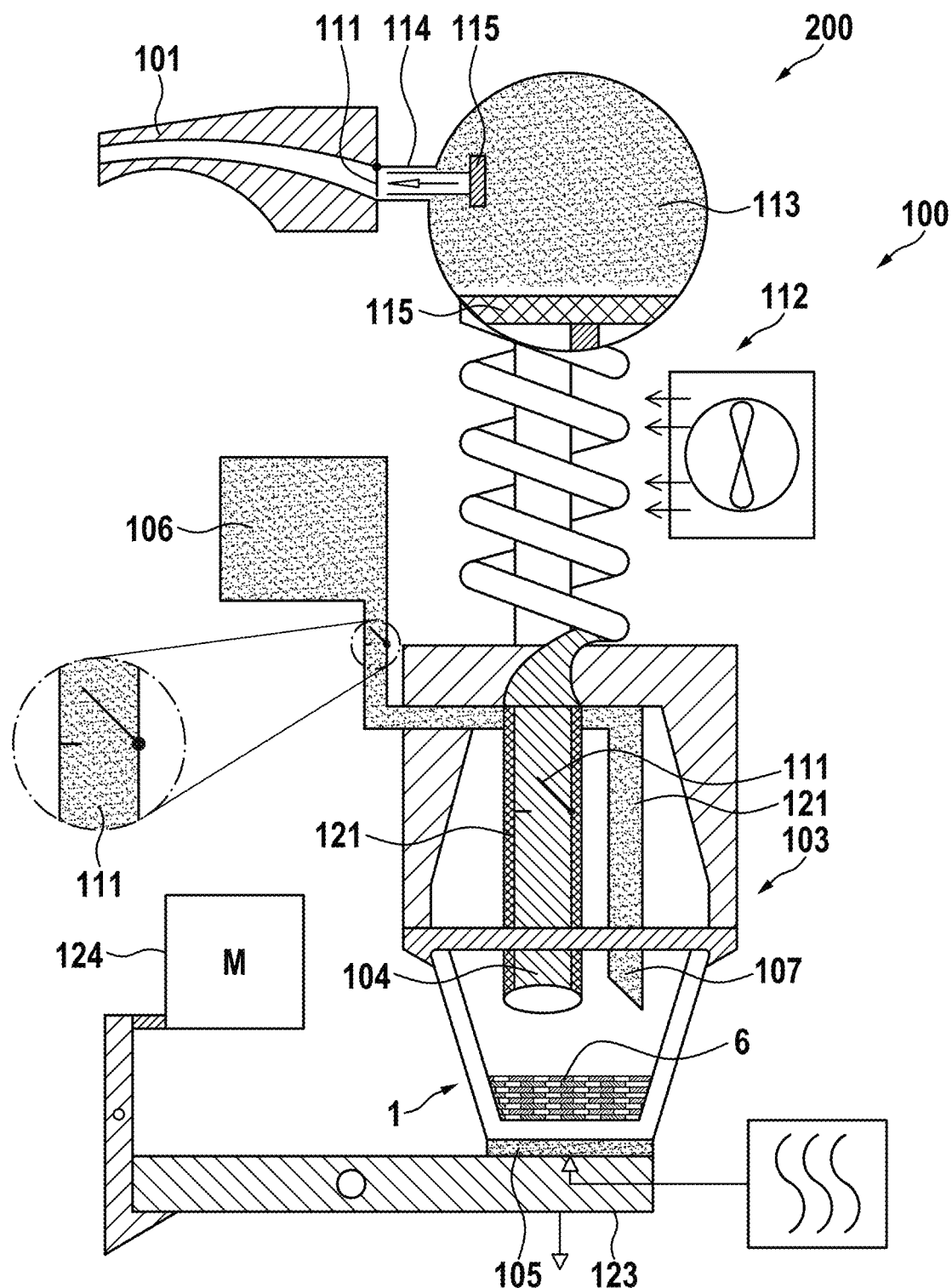
Figure 7:
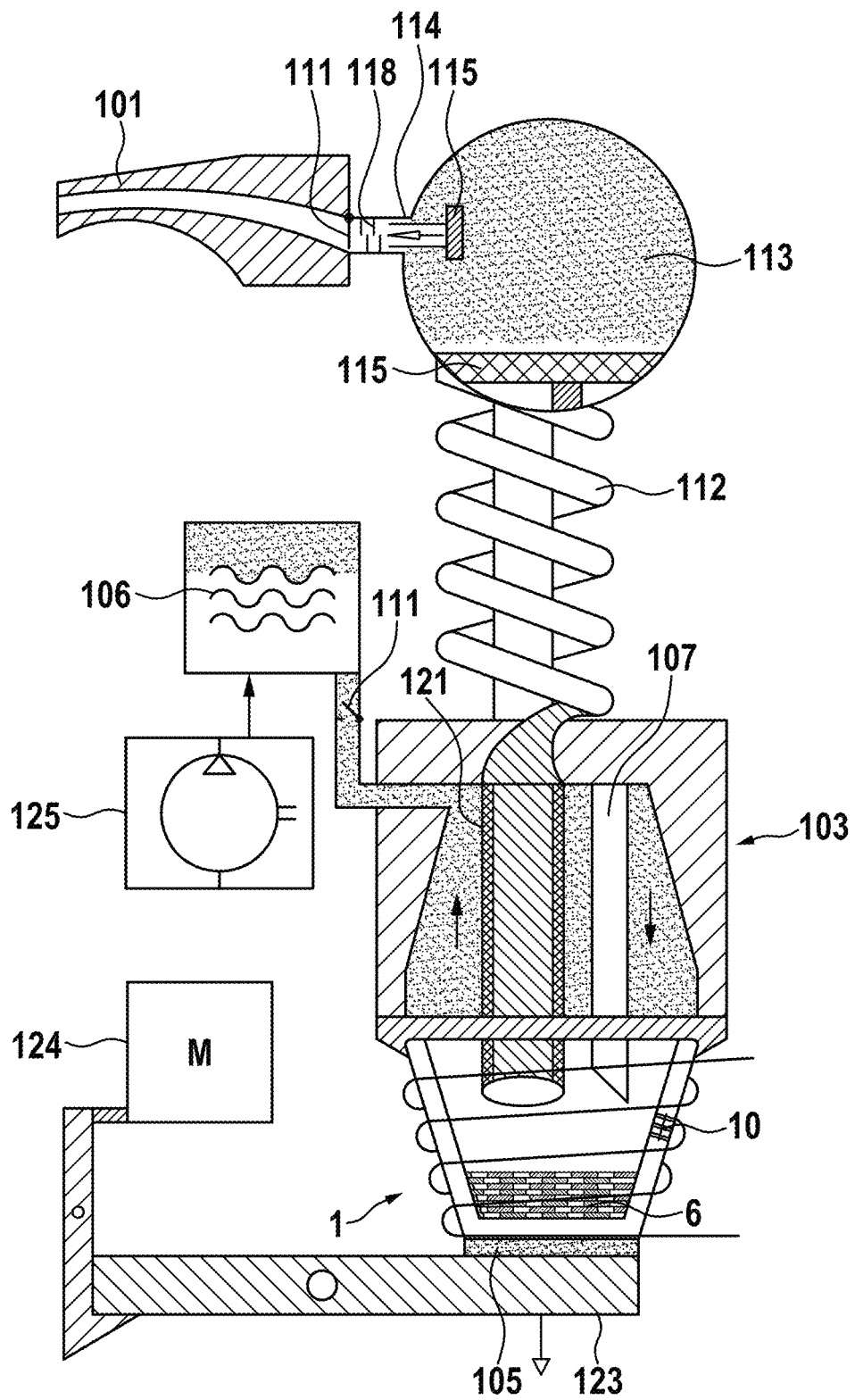
Figure 8:
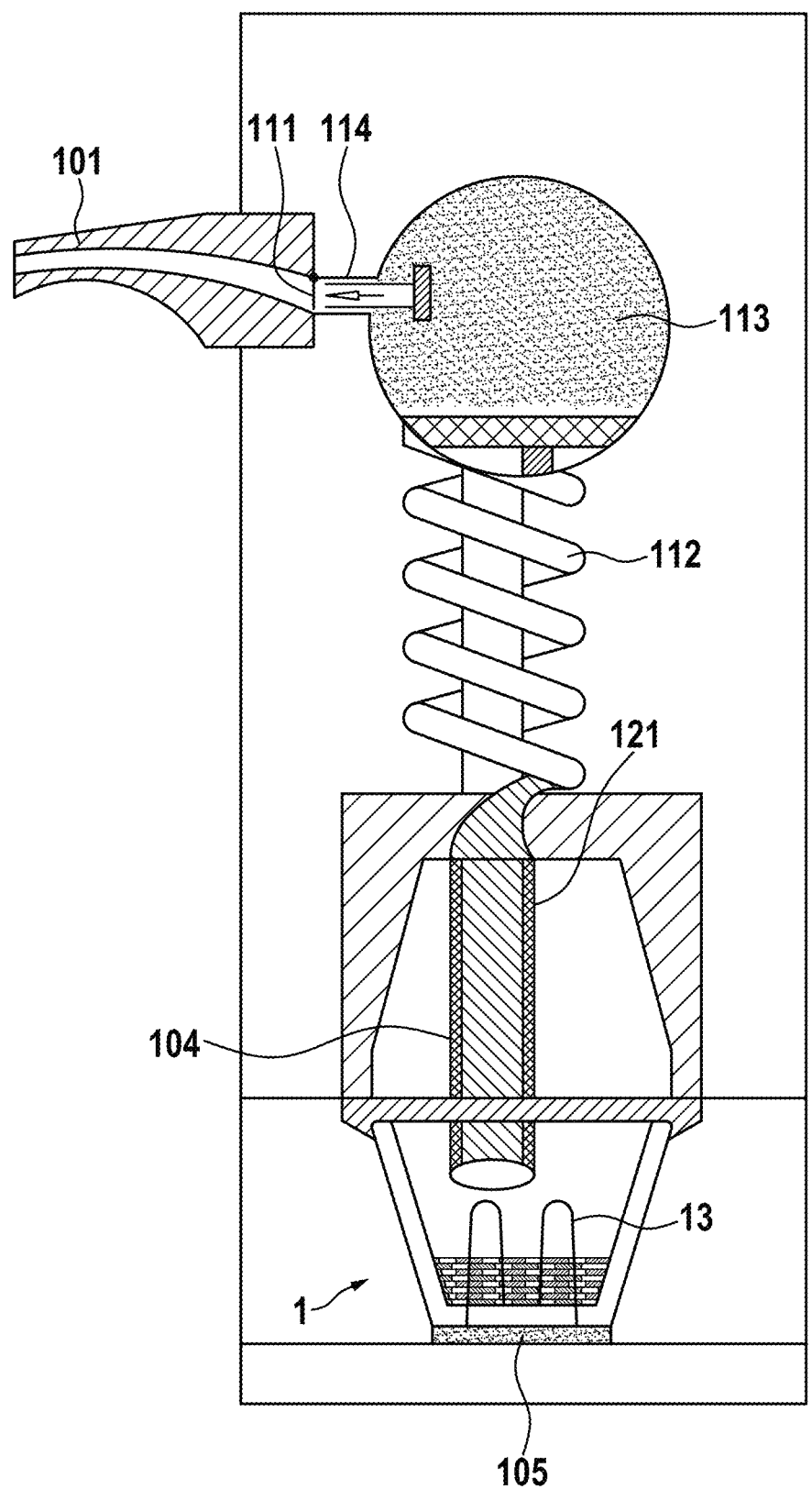
Figure 9:
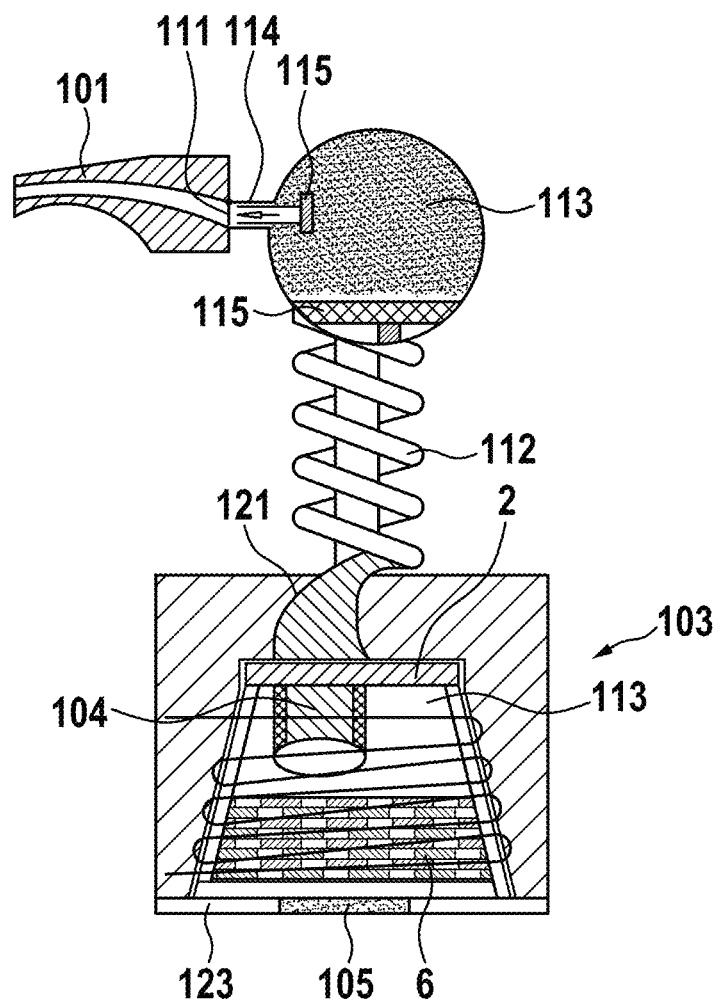
Figure 10:
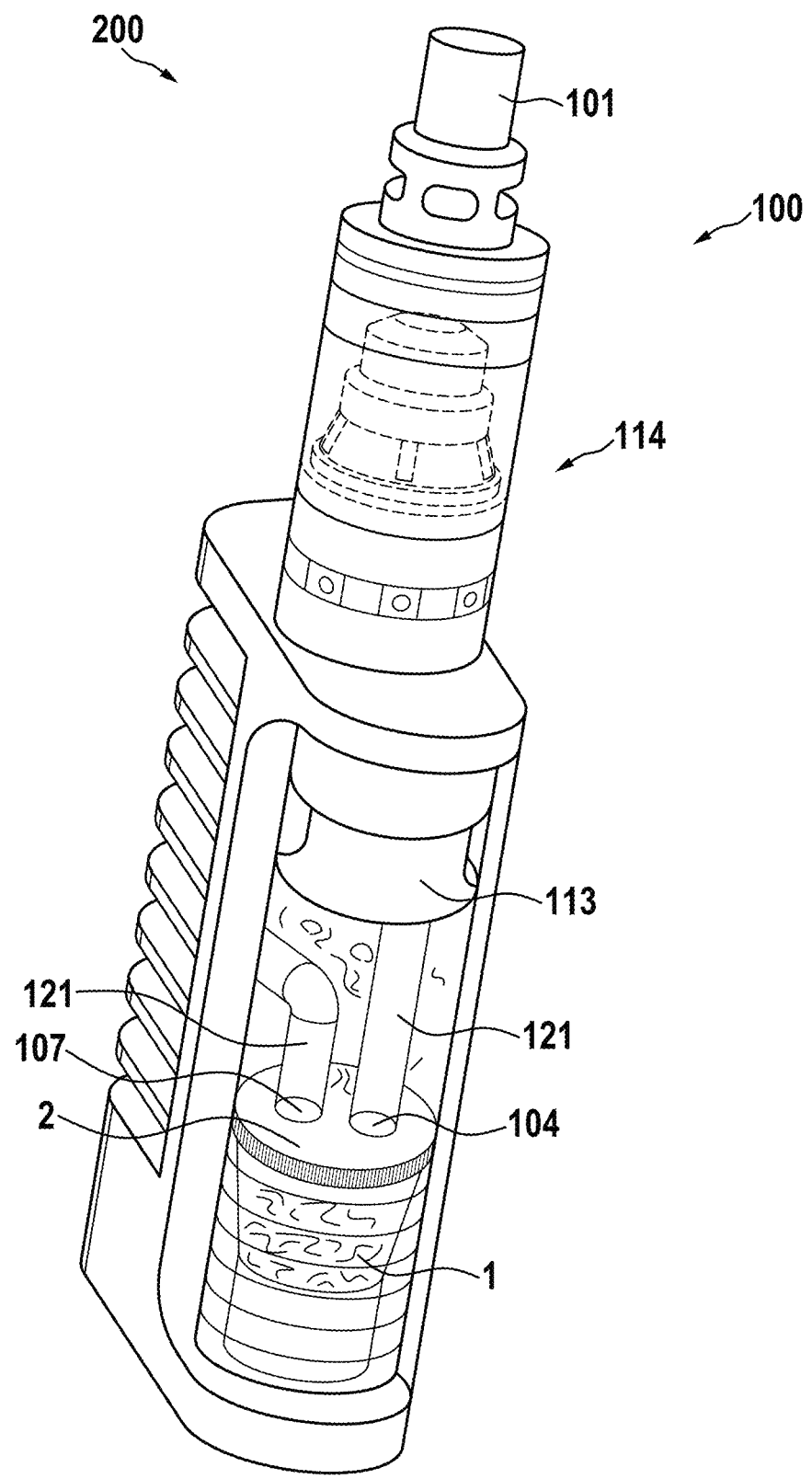
Figure 11:
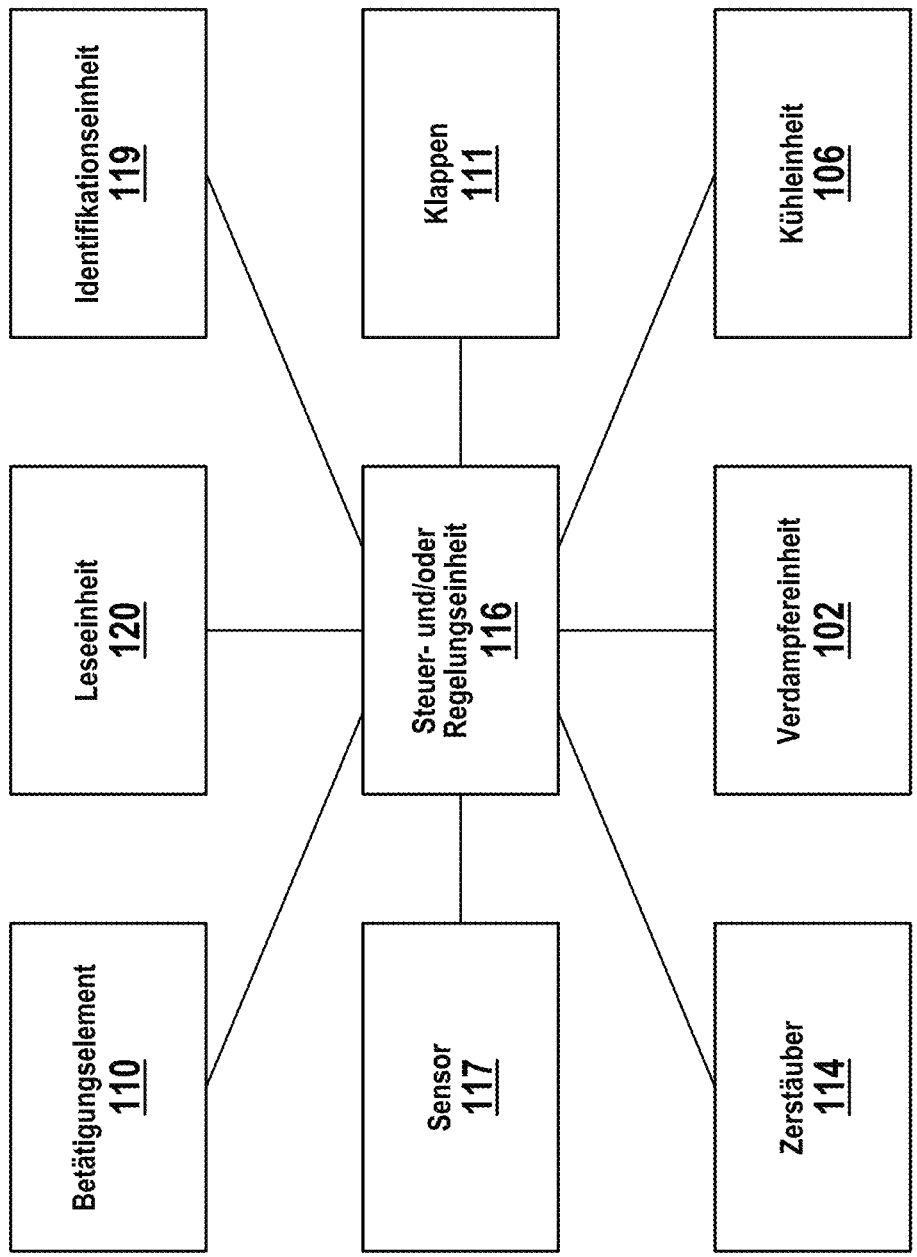

The invention is further explained with reference to the following figures. Thereby shows:

FIG. 1 an embodiment of a capsule according to the invention;

FIG. 2 another embodiment of a capsule according to the invention;

FIG. 3 still another embodiment of a capsule according to the invention;

FIG. 4 another embodiment of a capsule according to the invention;

FIG. 5 a vaporizer system with a vaporizer according to the invention and a capsule according to the invention received in the capsule receptacle;

FIG. 6 another vaporizer system with a vaporizer according to the invention and a capsule according to the invention received in the capsule receptacle;

FIG. 7 still another vaporizer system with a vaporizer according to the invention and a capsule according to the invention received in the capsule receptacle;

FIG. 8 still another vaporizer system with a vaporizer according to the invention and a capsule according to the invention received in the capsule receptacle;

FIG. 9 still another vaporizer system with a vaporizer according to the invention and a capsule according to the invention received in the capsule receptacle;

FIG. 10 still another vaporizer system in perspective view with a vaporizer according to the invention and a capsule according to the invention received in the capsule receptacle; and FIG. 11 schematic representation of the control and/or regulation unit and the components connected to it.

DETAILED DESCRIPTION

Example embodiments will now be described more fully with reference to the accompanying drawings.

FIG. 1 shows an embodiment of a capsule 1 according to the invention. The capsule 1 has a lid 2, side walls 3 and a bottom 4. The inner walls 7 of the side walls 3 and the inside of the lid 2 and the bottom 4 form a first cavity 5 in the interior of the capsule 1. The side walls 3 are of double-walled design, with an inner wall 7 facing the first cavity 5 and an outer wall 8 forming the outside of the side wall 3. A second cavity 9 is formed at least in sections between the inner wall 7 and the outer wall 8. The bottom 4 can also be of double-walled design, so that a second cavity 9 can also be formed at least in sections in the bottom. An active substance 6 is accommodated in the first cavity 5. An excipient 10 is accommodated in the second cavity. The inner wall 7 may be at least partially coated with a coating 11. Alternatively or additionally, the inside of the lid 2 and/or the bottom 4 may also be coated. The bottom 4 may, at least in sections, comprise or have a material that has a high thermal conductivity compared to the material of the side wall. The active ingredient 6 may be a plant-based active ingredient. Preferably, the active ingredient 6 is or comprises a cannabinoid. For example, the active ingredient 6 may be or comprise a cannabis flower, a cannabis extract, or a cannabis oil. The excipient 10 may have an active ingredient identical to the active ingredient 6. For example, both the active ingredient 6 and the excipient 10 may be or comprise ground cannabis flowers. However, the excipient 10 may also have an active ingredient that is different from the active ingredient 6, which may interact with the active ingredient 6 to produce a new effect, for example, or which may enhance or modify the effect of the active ingredient 6. The excipient 10 may comprise a chemical reactant. The chemical reactant may be adapted to react exothermically with a complementary chemical agent. The excipient 10 may comprise a flavoring agent, for example, to impart a fruit flavor to the vaporized active agent 6. However, the excipient 10 may alternatively or additionally be or comprise a food additive or dietary supplement.

The inner wall 7 can be semi-permeable, perforable and/or porous or have predetermined breaking points, at least in sections. In this way, a fluidic connection between the first and second cavities 5, 9 can be or is established. If the side wall 3 has one or more intermediate walls, the intermediate walls can also be semi-permeable, perforable and/or porous at least in sections or have predetermined breaking points.

The capsule 1 may have a coating 11 on an inner surface, for example of the inner wall 7 or the lid 2 or the bottom 4, at least in sections. The coating 11 may comprise, for example, a complementary chemical agent capable of reacting exothermically with the chemical reactant. It may also be provided that the inner surfaces of the first and/or second cavities 5, 9 comprise, at least in sections, a coating 11. In at least one embodiment, at least one inner side of the first cavity 5 has, at least in sections, a coating comprising a complementary chemical agent, wherein the excipient 10 comprises a chemical reaction agent in the second cavity 9 and a propellant gas is received in the second cavity 9. If the second cavity 9 is opened to the first cavity 5, for example by perforating the inner wall 7, the chemical reaction agent can be introduced into the first cavity 5 by the propellant gas and can react exothermically there with the complementary chemical agent, so that the active substance 6 is heated and vaporized.

Preferably, the capsule 1 may be impermeable to air, i.e., when the lid 2 is closed, the first and/or the second cavity 5, 9 may be fluidically separated from an environment of the capsule so that, for example, no air from the environment can enter the respective cavities. The lid 2 may be perforable. Alternatively, the lid 2 may be porous and/or semi-permeable. However, it may also be that the lid 2 comprises predetermined breaking points and/or valves. Thus, a fluidic connection of the first and/or second cavity 5, 9 through the lid 2 to the environment of the capsule 1 can be established.

The capsule 1, in particular the side walls 3 and/or the inner wall 7 and/or the outer wall 8, can at least partially consist of or comprise glass and/or a transparent plastic. This allows, for example, the state of the active ingredient 6 and/or the excipient 10 to be visible or examined from the outside without opening the capsule 1. It may be provided that the inner wall 7, the outer wall 8, the lid 2 and/or the bottom 4 comprise viewing windows. If both the inner wall 7 and the outer wall 8 have viewing windows, these may be arranged overlapping in a radial direction as viewed from a capsule axis, so that the first cavity 5 can be visible from the outside through the second cavity 9. It may be provided that the outside of the capsule, in particular any viewing windows that may be present, is at least partially coated with a UV filter. The outside of the capsule 1 may also be at least partially coated with a thermochromic material.

The capsule may be substantially cylindrical, conical, prismatic, truncated pyramidal, truncated pyramidal, cubic, cuboid, paraboloid, or the like.

FIG. 2 shows a further embodiment of a capsule 1 according to the invention. Compared with the embodiment shown in FIG. 1, the capsule has one or more grinding balls 12. The grinding balls 12 may be made of a ferromagnetic material so that they can be selectively moved by electromagnets, for example. As a result, the active substance 6 accommodated in the first cavity 5 of the capsule 1 can be comminuted by the movements of the grinding balls 12. It may also be provided that the grinding balls 12 may be heated, for example by induction, to vaporize or assist in vaporization of the active ingredient 6. The grinding balls 12 may have cut edges or the like.

FIG. 3 shows a further embodiment of a capsule 1 according to the invention. Compared with the embodiment shown in FIG. 1, the capsule has one or more heating coils 13. The heating coil 13 may be as shown in the figure, for example, spiral or wound. However, the heating coil 13 can also be a hot wire or a metal foil. When an electric current flows through the heating coil 13, it may heat up and thus vaporize the active ingredient 6 and/or the excipient 10. The capsule 1 may have contacts on an outer surface, for example on the bottom 4, for passing an electric current through the heating coil 13. It may be provided that the vaporizer 100 has contacts corresponding thereto in the capsule receptacle 103, so that when the capsule 1 is inserted, an electrical contact can be made and a current can flow through the heating coil 13.

FIG. 4 shows the lid 2 of a further embodiment of a capsule 1 according to the invention in a plan view. The lid 2 may be substantially circular, rectangular, elliptical or polygonal. A code 14, for example an alphanumeric code, a QR code, a barcode and/or a pictogram, is arranged on the lid 2. The code 14 may, for example, have or contain information relating to the contents of the capsule 1, for example relating to the composition and/or amount of the active ingredient 6 and/or the excipient 10 The code 14 may alternatively or additionally contain information relating to the vaporization process, for example a vaporization temperature and/or a temperature profile over time. Alternatively or additionally, the code 14 may contain information regarding a vaporizer type, an individual vaporizer, and/or a user, such that a particular capsule can only be used with a matching vaporizer type and/or an individual vaporizer and/or only by a particular user. Alternatively or additionally, the respective information may be stored on an RFID chip, RFID transponder or the like arranged on the outside of the lid 2 of the capsule 1. The vaporizer 100 may comprise a corresponding reading unit 120. The reading unit 120 may, for example, be arranged in the capsule receptacle 103 in such a way that, when the capsule 1 is inserted, the code 14 and/or the RFID chip can be detected or read. The reading unit 120 may detect the respective information, for example, optically or electromagnetically. The reading unit 120 may be connected to the control and/or regulation unit 116 of the vaporizer 100 for data exchange. This allows the control and/or regulation unit 116 to adjust, for example, the evaporation temperature and/or its variation over time based on the information detected by the reading unit 120. If, for example, deviations of the vaporizer type, the individual vaporizer and/or the user from the information contained in the code 14 or the RFID chip are detected by the control and/or regulating unit 116, it may be provided that the control and/or regulating unit 116 does not control or actuates the vaporizer unit 102, so that the active ingredient 6 and/or the excipient 10 is not vaporized or is only partially vaporized, and/or does not establish a fluidic connection between the first and/or second cavity 5, 9 and the mouthpiece 101. It may also be provided, for example, that the control and/or regulating unit 116 matches information contained in the code or RFID transponder relating to the active substance 6 and/or excipient 10 with an authorization control database connected to or associated with the control and/or regulating unit 116. In particular, in the medical application, this can be used to prevent an incorrect dosage or an overdose. In particular, this can also ensure that a patient can only vaporize or inhale the dosage, mixture and/or active ingredients intended for him.

FIG. 5 shows a partial section of an vaporizer 100 according to the invention with a capsule 1 according to the invention inserted in the capsule receptacle 103. In the embodiment example shown in FIG. 5, the lid 2 of the capsule 1 is perforated or pierced by the first capsule opening device 104 and the second capsule opening device 107. The capsule opening devices 104, 107 of FIG. 5 correspond to end pieces of connecting lines 121. Through the first capsule opening device 104, the first cavity 5 of the capsule 1 is fluidically connected via the cooling device 112 to the reservoir 113 and thus indirectly to the mouthpiece 101 not shown in FIG. 5. In the embodiment shown in FIG. 5, the first cavity 5 is fluidly connected to the reservoir 106 through the second capsule opening device 107. The capsule opening devices 104, 107 may, for example, have a cutting edge or be beveled to facilitate perforation of the lid 2. It may be provided that the first and/or second capsule opening devices 104, 107 are stationarily arranged in the vaporizer. Thereby, when the capsule 1 is inserted into the capsule receptacle 103, the movement of the capsule 1 relative to the first and/or second capsule opening device 104, 107 may cause the lid 2 to be perforated by the first and/or second capsule opening devices 104, 107. However, it may also be provided that the first and/or second capsule opening devices 104, 107 are movably arranged in the vaporizer 100 so that they are movable against the capsule 1 inserted in the capsule receptacle 103, so that the movement of the first and/or second capsule opening devices 104, 107 in the direction of the capsule 1 inserted in the capsule receptacle 103 perforates the lid 2. It may be provided that the movement of the first and/or second capsule opening device 104, 107 in the direction of the capsule receptacle 103 is initiated by an actuation of the actuation element 110 and/or occurs when the actuation element 110 is actuated.

It may be provided that the first and/or second capsule opening device 104, 107 is shaped or set up in such a way that, when the capsule 1 is inserted into the capsule receptacle 103, the inner wall 7 is opened by the first and/or second capsule opening device 104, 107 in such a way that a fluidic connection between the first cavity 5 and the second cavity 10 results. For example, the inner wall 7 may have predetermined breaking points suitable for this purpose. Alternatively or additionally, the inner wall 7 may be at least partially semi-permeable so that, for example, the vaporized auxiliary material 10 can pass through the inner wall in the direction of the first cavity 5 or can enter the cavity through the semi-permeable inner wall 7.

In the embodiment shown in FIG. 5, the vaporizer unit 2 comprises the reservoir 106. The reservoir 106 may have a chemical reactant stored therein. The capsule inner wall 7, the inner side of the lid 2 and or the bottom 4 and/or the connecting line between the first cavity 5 and the reservoir 106 may be coated in such a way that the chemical reactant reacts exothermically with the coating so that heat is released. The released heat may vaporize the active agent 6 and/or or the excipient 10 received in the first cavity 5 and/or received in the second cavity 9. The vaporized active ingredient 6 and/or the vaporized excipient 10 may be transferred to the reservoir 113 through the first capsule opening device 104, and may be cooled by the cooling device 112. The connecting lines 121 may include flaps 111 and/or valves to close or release fluidic communication between the interior of the capsule and the reservoir 113 and/or the reservoir 106. The flaps 111 and/or the valves may be controlled by a control and/or regulation unit 116. For example, it may be provided that after an actuation of an actuating element 110, the control and/or regulating unit 116 opens the flaps 111. Of course, the respective flaps 111 can be controlled individually by the open-loop and/or closed-loop control unit 116, e.g. opened and/or closed with a time delay.

For example, the reservoir 106 may be a replaceable cartridge. However, the reservoir 106 can also be a tank or container that is permanently installed in the vaporizer 100, preferably one that can be filled from the outside. The introduction of the fluid stored in the reservoir 106 through the second capsule opening device 107 into the capsule may, for example, be effected by gravity, optionally with the flap 111 open. However, it may also be provided to create or assist the introduction by positive pressure, for example by a pump, compressor or the like not shown in FIG. 5. It may also be provided to generate the overpressure, for example, by a compressed air impingement, a propellant gas or the like. For example, compressed air or a propellant gas can be introduced into the reservoir 106 via a further connection line 126 as indicated in FIG. 5, whereby the further connection line 126 can also have a flap 111 which can be controlled by the control and/or regulating unit 116. However, it can also be provided that no chemical reaction agent is stored in the reservoir, but for example compressed air or a propellant gas. In this case, the reservoir 106 is preferably a replaceable compressed air cartridge. By means of a hot wire 108, the compressed air or the propellant gas may be heated and, after being introduced into the capsule 1, may be arranged to vaporize the active ingredient 6 and/or the excipient 10. In this regard, the hot wire 108 may be arranged in the reservoir 106, the connecting line 121 and/or the second capsule opening device 107. Preferably, the compressed air is heated in such a way that its temperature is below the combustion temperature of the active substance 6 and/or of the excipient 10. This allows the active ingredient 6 and/or the excipient 10 to vaporize, but not to burn despite the supply of air. In addition to air, however, other suitable fluids and/or gases may also be used. If air is used, it may be envisaged that it is not held or provided in a reservoir 106, but is taken from the environment and/or drawn in from the environment and/or introduced into the vaporizer 100. For this purpose, the vaporizer 100 may comprise a fan or the like . . . . The ambient air may then be heated by the hot wire 108 and introduced into the capsule 1 via the second capsule opening device 107.

The cooling device 112 may be or include a cooling coil. Alternatively or additionally, the cooling device 112 may have cooling fins. It may also be provided that the cooling device 112 comprises a fan, for example a fan. Alternatively or additionally, the cooling device 112 may comprise evaporative cooling. It may be provided that the cooling device 112 is controllable by the control and/or regulation unit 116 so that the cooling capacity is variable or adjustable and can be regulated or controlled.

FIG. 6 shows another embodiment of an vaporizer 100 according to the invention with a capsule 1 according to the invention received in the capsule receptacle 103. The vaporizer unit 102 has a reservoir 106 with a chemical reactant described with reference to FIG. 5 above. In addition, the vaporizer unit 102 comprises a heating plate 105 contacting the bottom 4 of the capsule 1. The bottom 4 of the capsule 1 is preferably made of a material with a high thermal conductivity, so that heat can be conducted from the heating plate 105 to the inner side of the bottom 4 facing the interior of the capsule, so that the active ingredient 6 and the excipient 10 not shown in FIG. 6 can be vaporized. The heating plate 105 can be controlled by the control and/or regulation unit 116, so that the temperature of the heating plate 105 can be controlled and/or regulated. The heating plate 105 may be arranged in the capsule receptacle 103 such that it contacts the outer wall 8, the lid 2 or the bottom 4 of the capsule 1 when the capsule 1 is inserted.

The capsule 1 can be fixed in the capsule receptacle 103 by a pivotable plate 123 shown in FIG. 6. To insert the capsule 1 into the capsule receptacle 103, the plate 123 can be pivoted downward from the position shown in FIG. 6 and the capsule receptacle 103 can be opened. Alternatively or additionally, the plate 123 may be displaceable to open the capsule receptacle 103. The interlocking and/or displacement may be performed manually and/or by a swivel drive 124. Once the capsule 1 is inserted into the capsule receptacle 103 in its final position, the plate 123 may close the capsule receptacle 103 and form the bottom of the capsule receptacle 103. The heating plate 105 may be arranged on the plate 123 such that when the capsule receptacle 103 is closed, the heating plate 105 contacts the bottom 4 of the capsule 1, compare e.g. FIG. 6.

The cooling device 112 may include a fan, blower, or the like, as shown, for example, in FIG. 6. The vaporizer 100 may comprise a reservoir 113, an atomizer 114, and a mouthpiece 101. In the storage 113, already vaporized active substance 6 and/or vaporized auxiliary substance 10 can be kept in stock. Thus, vaporized active substance 6 and/or auxiliary substance 10 can also be provided during the "cold start" of the vaporizer. In addition, it can be provided, for example, that a sensor for measuring the concentration of the vaporized active ingredient 6 and/or auxiliary substance 10 is arranged by a flap 111 arranged upstream of the flap 111 arranged in the connecting line between the first capsule receptacle 104 and the reservoir 113, and the flap 111 is or is opened by the control and/or regulating unit 116 only if a predetermined concentration is or is exceeded. In this way, it can be ensured that a minimum concentration of active substance 6 and/or auxiliary substance 110 is always available at the mouthpiece 101. In this context, the storage 113 can be provided to buffer the active ingredient 6 and/or excipient 10 with a predetermined concentration, i.e., for example, to bridge supply gaps to lower concentrations, i.e., for example, when the flap 111 is closed. The reservoir 113 can also be used to homogenize the concentration of the active ingredient 6 and/or the excipient 10 before the mouthpiece. The accumulator 113 can also be heated and/or cooled.

An atomizer 114 is arranged between the mouthpiece 101 and the reservoir 113 in the embodiment shown in FIG. 6. A flap or valve or the like may be arranged between reservoir 113 and atomizer 114, so that a fluidic connection between reservoir 113 and atomizer 114 may be established or separated by the flap. Through the atomizer 114, the vaporized active ingredient 6 and/or excipient 10 may be dispersed into smaller droplets. The dispersed droplets may thereby have such a droplet distribution that they can, for example, penetrate well into the lungs of the user pulling or sucking on the mouthpiece 101 or are well passable through the lungs, which may result in a better absorption of the active substance 6 and/or the excipient 10 by the user. The vaporizer 100 may further comprise one or more filters 115.

The atomizer can atomize the vaporized active ingredient and/or excipient into intrathoracic (respirable) aerosol particles, where the particles can preferably have a diameter between about 0.5 and 5.5 μm.

By pulling the mouthpiece 101 and/or a positive pressure in the reservoir 113, a small concentrated amount of active ingredient 6 and/or excipient 10 can be aspirated and/or introduced into the atomizer 114 and/or the suction tube of the atomizer 114. The atomizer 114 and/or the suction tube may have a venturi nozzle and/or air channels, so that the venturi effect during suction dilutes and/or atomizes the concentrated aerosol accordingly. This can increase the proportion of the aerosol fraction that is respirable quite considerably. In order to filter large particles, it is conceivable to set the aspirated air in rotation so that the large particles are deposited on the porous wall of the suction tube or are filtered out and separated there. Appropriate filters can also be fitted in the suction tube, which also control the flow rate of the active ingredient 6 and/or the excipient 10 by their density. The aerosol flow in the suction tube can be diverted around via a kind of labyrinth or labyrinth-like channel 118 with at least one additional breakaway edge, whereby droplets that are too large are separated not only as a result of gravity but also by their contact at such a baffle as a result of the detour.

The nebulizer 114 may also be or include a nozzle nebulizer, an ultrasonic nebulizer, or a membrane nebulizer. In nozzle nebulizers, a strong stream of air creates a negative pressure at a nozzle, drawing droplets from a capillary system. As the droplets vary in size, a baffle plate holds back droplets that are too large. Ultrasonic nebulizers use a vibrating piezo crystal to generate ultrasound, which is responsible for the formation of the droplets. The higher the frequency is selected, the finer the droplets become. The frequency, for example, is 1-3 MHz. Membrane nebulizers are characterized by a very thin membrane consisting of a large number of micro-holes, which vibrates in the kHz range. Due to these oscillations, each microbore acts as a small pump and produces the finest droplets.

The vaporizer 100 may include an accumulator, not shown, that supplies electrical power to the control and/or regulating unit 116 and any other components housed within the vaporizer 100 that require power. The vaporizer 100 may include a connector on an exterior surface for a power cable to charge the accumulator. Alternatively or additionally, the accumulator may be replaceable. Alternatively or additionally, non-rechargeable batteries may be provided.

The vaporizer 100 may at least partially comprise or have a transparent plastic. Preferably, the vaporizer 100 may be made of or have a transparent plastic at least in the region of the capsule receptacle 103 and/or the capsule receptacle 103 itself, or at least be transparent so that a capsule 1 inserted into the capsule receptacle 103 is visible from outside the vaporizer 100.

FIG. 7 shows another embodiment of a vaporizer 100 according to the invention with a capsule 1 according to the invention received in the capsule receptacle 103. The vaporizer unit 102 has a reservoir 106 with a chemical reaction agent, wherein a pump 125 assists the penetration of the chemical reaction agent into capsule receptacle 103. As can be seen from FIG. 7, the vaporizer may be arranged such that the chemical reactant is not introduced into the interior of the capsule 1, but reacts outside the capsule 1 with the complementary chemical agent, which is present, for example, as a coating of the capsule receptacle 103 and/or the outside of the lid 2 of the capsule. In the embodiment shown in FIG. 7, the second capsule opening device 107 does not serve as a fluidic connection, but as a heat conductor for transporting the heat generated by the chemical reaction and may be designed, for example, as a solid metallic body or as a heat pipe. The second capsule opening device 107 may be dimensioned or shaped such that, when the capsule is inserted, the second capsule opening device 107 preferably contacts or penetrates the active ingredient 6 and/or the excipient 10 with its tip or an end portion. The second capsule opening device 107 may also be shaped or dimensioned such that, when the capsule is inserted by the second capsule opening device 107, the inner wall 107 is perforated and/or opened such that a fluidic connection is created between the first cavity 5 and the second cavity 10. However, it may alternatively or additionally be provided that the chemical reactant is guided in a heating coil not shown in FIG. 7 in the capsule receptacle 103, wherein the heating coil may be in contact with an outer surface of a capsule 1 inserted into the capsule receptacle 103. The heating coil may be tubular and coiled. The heating coil may be coated on its inner surface with a complementary chemical agent, such that the chemical reaction agent passed through the heating coil may react exothermically. The vaporizer unit 102 further comprises a heating plate 105 described with reference to FIG. 6. Further, the vaporizer unit 102 comprises a heating coil 109 disposed in the capsule receptacle 103, through which an electric current can flow and be heated. The heating coil 109 can heat and vaporize the active ingredient 6 and/or the excipient 10 accommodated in the capsule.

The vaporizer unit 102 may alternatively or additionally comprise a microwave generator not shown in FIG. 7. Advantageously, in this case, the active ingredient 6 and or excipient 10 contained in the capsule is moistened so that the active ingredient 6 and/or the excipient 10 can be heated and vaporized by the microwaves generated by the microwave generator.

FIG. 8 shows a further embodiment of an vaporizer 100 according to the invention with a capsule 1 according to the invention inserted in the capsule receptacle 103. The vaporizer unit 102 here has a heating plate 105 described above. Furthermore, a heating coil 13 is arranged in the first cavity 5 of the capsule 1, which can be heated by an electric current as described with reference to FIG. 3. This allows the active ingredient 6 and/or the excipient 10 not shown in FIG. 8 to be heated and vaporized. For example, the contacts of the heating coil 13 can be individually passed through the bottom 4 of the capsule and electrically conductively connected to corresponding contacts arranged on the plate.

The embodiment shown in FIG. 8 has only a first capsule opening device 104, but not a second capsule opening device. In this case, no external fluid is provided by the vaporizer unit 102 of the capsule 5. However, in some embodiments, a second capsule opening device may be provided as described above, and/or an external fluid, such as heated air from a reservoir or the environment may be provided into the capsule.

FIG. 9 shows another embodiment of a vaporizer unit 100 according to the invention and a capsule 1 according to the invention received in the capsule receptacle 103. The vaporizer unit 102 has a heating coil 109 arranged in the capsule opening 103 for heating the active substance 6 and/or the excipient 10 not shown in the figure received in the capsule. The vaporizer unit 102 also has a heating plate 105. The embodiment shown in FIG. 9 does not comprise a second capsule opening device. However, in some embodiments, a second capsule opening device may be provided as described above, and/or an external fluid, such as heated air from a reservoir or the environment, may be introduced into the capsule.

FIG. 10 shows a further embodiment of an vaporizer 100 according to the invention and a capsule 1 according to the invention received in the capsule receptacle 103 in a perspective view. In the embodiment shown, ambient air is introduced into the vaporizer 100, heated and supplied to the capsule 1 via the second capsule device 107. Heat transfer of the heated air to the active ingredient 6 and/or the excipient 10 vaporizes them. The vaporized active ingredient 6 and/or excipient 10 is passed through the second capsule opening device into the reservoir 113, where it is collected. The vaporized active ingredient 6 and/or excipient 10 is passed from the reservoir 113 through the atomizer 114, atomized in the atomizer 114, and then passed to the mouthpiece 101.

FIG. 11 schematically shows the control and/or regulation unit 116 and the elements or components connected thereto for data exchange. The term "connected for data exchange" can mean an exchange of information between the respective components. However, it can also be meant that the control and/or regulation unit 116 controls a respective component or transmits control commands. At least one sensor 117 is connected to the control and/or regulation unit 116. The open- and/or closed-loop control unit 116 may be or include a microcontroller, an integrated circuit, an FPGA, and/or a processor or the like. The control-and-or-regulation unit 116 may include a data memory in which information regarding, for example, the type of vaporizer, the individual vaporizer, and/or an individual user may be stored.

The at least one sensor 117 may be or comprise a temperature sensor, a pressure sensor, a sensor for measuring the flow velocity and/or a sensor for measuring the concentration of, for example, the active ingredient 6. At least one sensor 117 may be arranged in each of the first and/or second cavity 5, 9 of the capsule 1, the first and/or second capsule opening device 104, 107, the capsule receptacle 103, the reservoir 106, the respective connecting lines 121, the cooling unit 112, the reservoir 113, the atomizer 114, and/or the mouthpiece 101. The measured values measured by the at least one sensor 117 can be transmitted to the control and/or regulation unit 116 and evaluated by the latter. The actuating element 110, the reading unit 120 and/or the identification unit 119 may be connected to the control and/or regulation unit 116 and the acquired information, e.g. actuation of the actuating element, acquired code 14 or user identification information may be transmitted to and evaluated by the control and/or regulation unit 116. Preferably, the identification unit 119 may be or comprise a fingerprint sensor 119. The control and/or regulation unit 116 may control the vaporizer unit 102, the cooling unit 106, the flaps 111, and/or the atomizer 114.

The control may depend on the evaluation of the measured values and/or transmitted information and/or the information stored in the data memory performed by the control and/or regulation unit 116. If the code 14 contains, for example, information relating to the active ingredient 6, it may be provided that the open-loop and/or closed-loop control unit 116 determines an evaporation temperature from a database stored in its data memory and controls the evaporation unit 102 and/or the cooling unit 112 in such a way that the evaporation temperature is reached and/or maintained and/or not exceeded. Similarly, for example, the evaporating temperature may also be directly included in the code 14 and evaluated by the control and/or regulation unit 116. In some embodiments, for example, alternatively or additionally, information contained in the code 14 regarding the active agent 6 and/or the excipient 10 may be compared to the information of the individual user stored in the data memory to determine an authorization of the user to vaporize the active agent 6 and/or the excipient 10. If the user is not authorized, it may be provided that the control and/or regulation unit 116 does not control the vaporizer unit 102 and/or the flaps 111 so that the active agent 6 and/or the excipient 10 is not vaporized. For example, if the active ingredient 6 is or contains a drug to be vaporized, it can be ensured that the user does not ingest an incorrect or non-prescribed drug through the vaporizer 100 and/or that the dosage of the drug is the same as that prescribed. Similarly, the fingerprints captured by the fingerprint sensor 119 can be compared with information stored in the data memory regarding the individual user, so that the vaporizer can be used, for example, only by one or possibly several specific users. This may result in better hygiene in particular. It may be provided that the vaporizer 100 has a signal element, for example an LED, on an outer side, which signals unauthorized use or non-vaporization of the active ingredient 6 and/or the excipient 10. In some embodiments, the LED may also be configured to indicate, for example, a fill level of an accumulator of the vaporizer 100 or the like.

The features disclosed in the claims, the description, the figures and the abstract may be essential to the invention individually or in combination.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity; and wherein the bottom of the capsule includes, at least on its outer side, at least partially a material having a higher thermal conductivity compared to the material of the side wall.

2. The capsule according to claim 1, wherein the outer wall, the lid and the bottom are air impermeable, so that the first and/or the second cavity is hermetically sealed against an environment of the capsule.

3. The capsule according to claim 1, wherein the first and/or the second cavity is either evacuated or at least partially filled with an inert gas.

4. The capsule according to claim 1, wherein the inner wall of the side wall arranged between the first and second cavities is perforable, porous and/or semi-permeable and/or has predetermined breaking points.

5. The capsule according to claim 1, wherein the lid is perforable and/or has predetermined breaking points and/or valves.

6. The capsule according to claim 1, wherein the active ingredient and/or the excipient is or comprises a cannabis flower, a cannabis oil, a cannabinoid, or a cannabis extract.

7. The capsule according to claim 1, wherein the lid and/or the bottom on an inner side facing the cavity and/or the inner wall at least partially comprises a coating, the coating preferably comprising a chemical reactant, a UV filter and/or a thermochromic material.

8. The capsule according to claim 1, wherein one or more grinding balls for grinding the active substance are accommodated in the first cavity, wherein the grinding balls comprise a ferromagnetic material.

9. The capsule according to claim 1, wherein the inner wall and/or the outer wall consists of or comprises, at least in sections, a glass and/or a transparent plastic.

10. The capsule according to claim 1, wherein a heating coil is arranged in the first cavity and/or the second cavity.

11. The capsule according to claim 1, wherein on the outside of the lid and/or the bottom of the capsule there is a QR code, an alphanumeric code, a barcode and/or a pictogram, and/or an RFID chip.

12. A vaporizer for vaporizing active substances, having a mouthpiece and a vaporizer unit, wherein the vaporizer has a capsule receptacle for receiving a capsule according to claim 1, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated.

13. The vaporizer according to claim 12, wherein the vaporizer unit is or comprises a heating plate in the capsule receptacle, such that when the capsule is accommodated, the heating plate contacts an outside, preferably a bottom of the capsule.

14. The vaporizer of claim 12, wherein the vaporizer unit is or comprises a reservoir for containing a fluid, the reservoir being fluidically connected to the capsule receptacle via a second capsule opening device such that, when the capsule is received, fluidic communication can be provided between a cavity of the capsule and the reservoir by the second capsule opening device; and a. one or more heating wires in the reservoir and/or fluidically between the reservoir and the capsule receptacle for heating the fluid and/or b. the fluid is received in the reservoir, the fluid being or comprising a chemical reactant such that heat is released by a chemical reaction of the chemical reactant with a complementary chemical agent.

15. The vaporizer of claim 12, wherein the vaporizer unit is or comprises a microwave generator.

16. The vaporizer of claim 12, wherein the vaporizer unit is or comprises a heating coil in the capsule receptacle.

17. The vaporizer of claim 12, wherein the vaporizer comprises an actuator a. having flaps which are opened when the actuating element is actuated and/or
b. being moved in the direction of the capsule receptacle when the actuating element is actuated.

18. The vaporizer according to claim 12, wherein the vaporizer comprises a cooling unit fluidically arranged between the capsule receptacle and the mouthpiece, such that active substance vaporized by the vaporizer is cooled, preferably to a temperature of 10-30° C., particularly preferably to a temperature of 15-25° C.

19. The vaporizer of claim 12, wherein the vaporizer comprises a reservoir fluidically upstream of the mouthpiece, in which reservoir active substance vaporized by the vaporizer can be collected.

20. The vaporizer of claim 12, wherein the mouthpiece comprises an atomizer for atomizing vaporized active agent into droplets.

21. The vaporizer according to claim 12, wherein the mouthpiece, the atomizer and/or the second capsule orifice device is or comprises a venturi nozzle and/or has a hyperbolic cross-section in the flow direction.

22. The vaporizer of claim 12, wherein the vaporizer comprises at least one filter fluidically upstream of the mouthpiece, the filter being disposed on the mouthpiece.

23. The vaporizer according to claim 12, wherein the vaporizer comprises a control and/or regulation unit and at least one sensor, preferably a temperature sensor, for controlling and regulating the temperature of the vaporizer unit.

24. The vaporizer of claim 12, wherein the atomizer comprises a labyrinthine channel having at least one breakaway edge such that droplets flowing through the channel can be separated larger than a maximum droplet size.

25. The vaporizer according to claim 12, comprising a fingerprint sensor, wherein the fingerprint sensor is arranged such that when the vaporizer is used with one hand, the fingerprint sensor detects a fingerprint.

26. The vaporizer according to claim 12, which has a reading unit, the reading unit being set up to detect and/or read a code, preferably a QR code, an alphanumeric code, a barcode and/or a pictogram, and/or RFID chip, applied to an outer side of the capsule when the capsule is inserted, the reading unit preferably being arranged in the capsule receptacle.

27. A vaporizer system for vaporizing an active ingredient, comprising a vaporizer according to claim 12 and a capsule according to claim 1 received in the capsule receptacle of the vaporizer.

28. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
an actuator:
a. having flaps which are opened when the actuating element is actuated and/or
b. being moved in the direction of the capsule receptacle when the actuating element is actuated.

29. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
a cooling unit fluidically arranged between the capsule receptacle and the mouthpiece, such that active substance vaporized by the vaporizer is cooled, preferably to a temperature of 10-30° C., particularly preferably to a temperature of 15-25° C.

30. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
wherein the mouthpiece, the atomizer and/or the second capsule orifice device is or comprises a venturi nozzle and/or has a hyperbolic cross-section in the flow direction.

31. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
  wherein on the outside of the lid and/or the bottom of the capsule there is a code, an alphanumeric code, a barcode and/or a pictogram, and/or an RFID chip: and
  wherein the vaporizer comprises at least one filter fluidically upstream of the mouthpiece disposed on the mouthpiece.

32. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
  a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
  wherein the vaporizer comprises a control and/or regulation unit and at least one sensor, preferably a temperature sensor, for controlling and regulating the temperature of the vaporizer unit.

33. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
  a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
  a fingerprint sensor, wherein the fingerprint sensor is arranged such that when the vaporizer is used with one hand, the fingerprint sensor detects a fingerprint.

34. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
  a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
  a reading unit, the reading unit being set up to detect and/or read a code, preferably a QR code, an alphanumeric code, a barcode and/or a pictogram, and/or RFID chip, applied to an outer side of the capsule when the capsule is inserted, the reading unit preferably being arranged in the capsule receptacle.

35. A vaporizer system for vaporizing an active ingredient, comprising:
  a capsule having at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
  a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated.

36. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity; and
  wherein one or more grinding balls for grinding the active substance are accommodated in the first cavity, wherein the grinding balls comprise a ferromagnetic material.

37. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity; and
    a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated.

38. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
    a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
    wherein the vaporizer comprises a reservoir fluidically upstream of the mouthpiece, in which reservoir active substance vaporized by the vaporizer can be collected.

39. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
    a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
    wherein the mouthpiece comprises an atomizer for atomizing vaporized active agent into droplets.

40. A capsule for use in a vaporizer comprising at least one first cavity formed at least partially by a lid, side walls and a bottom of the capsule, and a vaporizable active substance accommodated in the first cavity of the capsule, wherein the side walls and/or the bottom are designed to be double-walled at least in sections, with an inner wall facing the first cavity of the capsule and an outer wall facing the outside of the capsule, so that at least one second cavity is formed between the inner wall and the outer wall, wherein an excipient, a chemical reaction agent and/or a flavoring agent is accommodated in the second cavity;
    a mouthpiece and a vaporizer unit, wherein the vaporizer has a capsule receptacle for receiving the capsule, the capsule receptacle having a first capsule opening device and being fluidically connected to the mouthpiece via the first capsule opening device, so that, when the capsule is accommodated, a fluidic connection between a cavity of the capsule and the mouthpiece can be provided by the first capsule opening device, wherein the vaporizer unit is arranged for vaporizing an active substance located in the cavity of the capsule when the capsule is accommodated; and
    wherein the atomizer comprises a labyrinthine channel having at least one breakaway edge such that droplets flowing through the channel can be separated larger than a maximum droplet size.

\* \* \* \* \*